(12) United States Patent
Leussler et al.

(10) Patent No.: US 10,534,049 B2
(45) Date of Patent: Jan. 14, 2020

(54) RADIO FREQUENCY VOLUME COIL WITH IMPROVED SPACE AND ACCESS FOR USE IN A MAGNETIC RESONANCE EXAMINATION SYSTEM

(71) Applicant: KONINKLIJKE PHILIPS N.V., Eindhoven (NL)

(72) Inventors: Christoph Leussler, Eindhoven (NL); Christian Findeklee, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 27 days.

(21) Appl. No.: 15/569,412

(22) PCT Filed: Apr. 26, 2016

(86) PCT No.: PCT/EP2016/059253
§ 371 (c)(1),
(2) Date: Oct. 26, 2017

(87) PCT Pub. No.: WO2016/174012
PCT Pub. Date: Nov. 3, 2016

(65) Prior Publication Data
US 2018/0299521 A1 Oct. 18, 2018

(30) Foreign Application Priority Data
Apr. 30, 2015 (EP) .................................... 15166023

(51) Int. Cl.
*G01R 33/34* (2006.01)
*G01R 33/422* (2006.01)
(Continued)

(52) U.S. Cl.
CPC ........ *G01R 33/34076* (2013.01); *A61B 5/055* (2013.01); *G01R 33/422* (2013.01); *G01R 33/4808* (2013.01)

(58) Field of Classification Search
CPC ............ G01R 33/34076; G01R 33/422; G01R 33/4808; A61B 5/55
See application file for complete search history.

(56) References Cited

U.S. PATENT DOCUMENTS

| | | |
|---|---|---|
| 4,680,548 A | 7/1987 | Edelstein et al. |
| 4,740,752 A | 4/1988 | Arakawa et al. |
| (Continued) | | |

*Primary Examiner* — Dominic E Hawkins

(57) ABSTRACT

A radio frequency volume coil (136; 236) for use in a magnetic resonance examination system (10) includes a radio frequency shield (148; 248), and a pair of radio frequency conductive loop members (138; 238) spaced along a common longitudinal axis (140; 240), a plurality of axially arranged radio frequency conductive members electrically connected to at least one of the radio frequency conductive loop members (138; 238). At least two axially arranged loop coil interconnecting radio frequency conductive members (114; 244) electrically interconnect the radio frequency conductive loop members (138; 238). At least two of the axially arranged shield connecting radio frequency conductive members are axially arranged in an aligned manner at an azimuthal position within a range between azimuthal positions of the at least two loop coil interconnecting members (144; 244), and electrically serve and connect one of the two radio frequency conductive loop members (138; 238) to the radio frequency shield (148; 248). At least one installation space (152; 252) within an inner volume of the radio frequency volume coil (136; 236) is accessible from outside the radio frequency volume coil (136; 236) at least in a radial direction (56) within the range between the azimuthal positions of the two loop coil interconnecting members (144; 244) and within a range of axial directions between axial positions of ends of the shield-connecting members (146; 246) that are distal to the radio frequency conductive loop member (138; 238).

17 Claims, 3 Drawing Sheets

(51) Int. Cl.
*G01R 33/48* (2006.01)
*A61B 5/055* (2006.01)

(56) References Cited

U.S. PATENT DOCUMENTS

| | | | |
|---|---|---|---|
| 4,837,515 A | 6/1989 | Nishihara et al. | |
| 5,998,999 A | 12/1999 | Richard et al. | |
| 8,022,705 B2 | 9/2011 | Bogdanov | |
| 8,786,283 B2 | 7/2014 | Gross et al. | |
| 2008/0197848 A1* | 8/2008 | Zhai | G01R 33/34046 324/318 |
| 2009/0206836 A1 | 8/2009 | Eberler et al. | |
| 2010/0036237 A1* | 2/2010 | Eberlein | G01R 33/34046 600/411 |
| 2010/0073000 A1* | 3/2010 | Ludwig | G01R 33/34061 324/318 |
| 2012/0169341 A1* | 7/2012 | McKinnon | A61B 6/037 324/318 |
| 2012/0253174 A1* | 10/2012 | Popescu | A61B 6/037 600/411 |
| 2014/0247050 A1* | 9/2014 | Tomiha | G01R 33/34092 324/322 |
| 2014/0266206 A1 | 9/2014 | Dempsey et al. | |

* cited by examiner

RADIO FREQUENCY VOLUME COIL WITH IMPROVED SPACE AND ACCESS FOR USE IN A MAGNETIC RESONANCE EXAMINATION SYSTEM

CROSS-REFERENCE TO RELATED APPLICATIONS

This application is a U.S. national phase application of International Application No. PCT/EP2016/059253, filed on Apr. 26, 2016, which claims the benefit of EP Application Serial No. 15166023.0 filed on Apr. 30, 2015 and is incorporated herein by reference.

FIELD OF THE INVENTION

The invention pertains to a radio frequency volume coil for use in a magnetic resonance examination system, and a magnetic resonance examination system with such radio frequency volume coil.

BACKGROUND OF THE INVENTION

In the art of magnetic resonance examination, the birdcage resonator, also known as birdcage coil, is a well-known volume radio frequency coil design for generating a radio frequency magnetic excitation field $B_1$ to be applied to nuclei of or within a subject of interest for magnetic resonance excitation, wherein the subject of interest is positioned at least partially within the birdcage coil, which in turn is arranged within a static, homogeneous magnetic field $B_0$ arranged substantially perpendicular to the radio frequency magnetic excitation field $B_1$.

In the art, birdcage resonators are known to serve as radio frequency transmit coils and/or radio frequency receive coils. They are usually operated in resonance at a radio frequency corresponding to the Larmor frequency, which depends on the strength of the static magnetic field $B_0$ and the gyromagnetic magnetic ratio of the species of nuclei under consideration.

U.S. Pat. No. 4,680,548 describes the volume radio frequency coil design, later referred to as the "birdcage coil" for its appearance, as a magnetic resonance radio frequency coil having a pair of conductive loop elements spaced along a common longitudinal axis. Each of the loop elements may include a plurality of serially-connected capacitive elements spaced along the loop peripheries. A plurality of axial conductive elements (commonly referred to as "rungs") electrically interconnect the conductive loop elements at points between adjacent ones of the serially connected capacitive elements. In the high-pass embodiment of the radio frequency coil, the axial conductive segments may be wires, conducting tubes or flat conductive tapes whose inherent inductance is needed for proper coil operation. A band-pass embodiment of the coil is realized by including capacitive elements in each of the axial conductive segments. Birdcage coils are known to have as many resonant modes as there are radial or axial conductive segments. The preferred excitation mode for the birdcage coil is the one in which a generated radio frequency magnetic excitation field $B_1$, when operated as a transmit coil, is as homogenous as possible. This is the case for resonant modes whose current distribution in the rungs is proportional to sin θ or cos θ, respectively, wherein θ denotes the azimuthal angle measured circumferentially about the birdcage coil axis.

U.S. Pat. No. 4,680,548 further describes to operate the birdcage coil in a quadrature excitation mode in which the birdcage coil transmits a circularly polarized radio frequency magnetic field, known to maximally interact with nuclei spins. To this end, the birdcage coil is excited at two input capacitors located at right angles relative to one another, for instance along the circumference of one of the conductive loop elements, by two radio frequency sources that are electrically 90° out of phase relative to one another. In the case of quadrature excitation, the magnitude of the currents in each rung is equal while the relative phase angle increments in a linear manner with the azimuthal angle θ.

US patent application publication US 2010/0036237 A1 describes a detector unit for arrangement in a field generating unit of a magnetic resonance device. The detector unit has an RF transmission/reception system for transmitting RF pulses into, or receiving magnetic resonance signals from, an examination volume of the field generation unit. The RF transmission/reception system surrounds a patient tunnel at a radial distance from a tunnel axis thereof, and is divided into two sub-systems located at an axial distance between 10 cm to 50 cm from each other along the direction of the tunnel axis, so as to form a substantially annular cavity or interstice therebetween. Each one of the sub-systems is fashioned as semi-birdcage resonator, each semi-birdcage resonator comprising a ferrule and a ring and a number of antenna rods that start from the respective ferrule and are connected with their ends at the ring that forms part of an RF shield.

U.S. Pat. No. 4,837,515 A describes a radio frequency coil for nuclear magnetic resonance imaging that comprises two annular conductors which are coaxially disposed at opposite ends of a prescribed axis and at least one pair of longitudinal conductor groups which are symmetrically disposed in parallel to the prescribed axis and extend longitudinally from one annular conductor to the other. Each longitudinal conductor group comprises a plurality of longitudinally extending electrical conductors whose ends are secured and electrically connected to the annular conductors. The longitudinal conductors are preferably in the form of electrically conducting wires, tubes, or plates. The annular conductors can be in the form of one-piece rings or in the form of one or more pairs of arcuate plates which are electrically connected with one another and disposed about the prescribed axis in the form of a ring. In one embodiment, one of the longitudinal conductor groups of each pair is transversely divided in two at its mid portion. The lower ends of the longitudinal conductors in the upper half of the divided longitudinal conductor group are short-circuited, and similarly the upper ends of the longitudinal conductors in the lower half of the divided longitudinal conductor group are short circuited by suitable means. The two halves are connected with one another by capacitive coupling.

SUMMARY OF THE INVENTION

The radio frequency magnetic excitation field of radio frequency volume coils of the birdcage coil design is known to be the more homogeneous the higher the number of rungs. With an increasing number of rungs it becomes more and more difficult to position auxiliary devices such as amplifiers as close to the radio frequency volume coil as desired, and access to the subject of interest positioned within the radio frequency volume coil during examination for monitoring and/or therapy purposes becomes more and more restricted.

It is therefore desirable to have a radio frequency volume coil with the beneficial properties of providing a homogeneous radio frequency magnetic excitation field $B_1$ but with improved access to the subject of interest positioned within the radio frequency volume during examination and providing options of positioning auxiliary devices close to the radio frequency volume coil.

It is therefore an object of the invention to provide a radio frequency volume coil for use in a magnetic resonance examination system having such properties.

In one aspect of the present invention, the object is achieved by a radio frequency volume coil for use in a magnetic resonance examination system, for at least one out of generating a radio frequency magnetic excitation field $B_1$ to be applied to nuclei of or within a subject of interest to be examined and acquiring magnetic resonance signals from the excited nuclei, wherein the radio frequency volume coil comprises a radio frequency shield, a pair of radio frequency conductive loop members spaced along a common longitudinal axis and a plurality of axially arranged radio frequency conductive members electrically connected to at least one of the radio frequency conductive loop members.

At least two axially arranged radio frequency conductive members of the plurality of axially arranged radio frequency conductive members electrically interconnect the radio frequency conductive loop members, serving as an interconnecting member. The at least two axially arranged radio frequency conductive members are positioned at two different azimuthal positions with regard to the common longitudinal axis, defining a range between the two different azimuthal positions that is less than or equal to 180°.

At least two of the axially arranged radio frequency conductive members of the plurality of axially arranged radio frequency conductive members are axially arranged in an aligned manner at an azimuthal position within the range between the two different azimuthal positions of the at least two interconnecting members, and electrically serve as shield-connecting members. Each shield-connecting member provides a radio frequency connection for one of the two conductive loop members to the radio frequency shield.

The phrases "radio frequency connection" and "radio frequency conductive", as used in this application, shall be understood particularly as an electrical connection that enables the flow of electrical currents at radio frequencies without the use of a galvanic connection. For reasons of briefness, the term "conductive", as used in this application, shall be understood as radio frequency conductive if not explicitly defined differently.

The radio frequency volume coil further includes at least one installation space within an inner volume of the volume coil that is accessible between the axially arranged radio frequency conductive members from outside the volume coil at least in a radial direction with regard to the common longitudinal axis within the range between the two different azimuthal positions of the two interconnecting members, and within a range of the axial direction between axial positions of ends of the shield-connecting members that are distal to the radio frequency conductive loop member they are connected to.

The phrase "inner volume", as used in this application, should be understood particularly as the space surrounded by the pair of radio frequency conductive loop members and the plurality of axially arranged radio frequency conductive members.

One advantage lies in that the at least one installation space that is created by the disclosed arrangement of the plurality of axially arranged radio frequency conductive members provides improved access to the subject of interest positioned within the radio frequency volume during examination, while at the same time the beneficial properties of the radio frequency volume coil with regard to homogeneity of a generated radio frequency magnetic excitation field $B_1$ and/or a homogeneous sensitivity for acquiring magnetic resonance signals from excited nuclei of or within the subject of interest can be maintained.

Another advantage lies in that the at least one installation space provides options for positioning auxiliary devices close to the radio frequency volume coil.

Yet another advantage lies in that the at least one installation space, in a suitable embodiment, may increase a space available for positioning the subject of interest within the volume coil, for instance for the elbow region, by which an increased comfort for the subject of interest can be achieved, which in turn is known to be beneficial with regard to uninterruptedly carrying out a magnetic resonance examination.

Preferably, each conductive loop member of the pair of conductive loop members has an elliptical, in particular a circular shape, but also other shapes for the loop members, such as polygonal shapes, in particular an octagonal shape, are contemplated.

In a preferred embodiment, the axially arranged conductive members of the plurality of axially arranged conductive members are regularly spaced in the azimuthal direction about the common longitudinal axis. In this way, a high degree of homogeneity in generating a radio frequency magnetic excitation field $B_1$ and/or a high degree of homogeneity regarding a sensitivity of receiving magnetic resonance signals from excited nuclei of or within the subject of interest can be facilitated.

In another preferred embodiment, at least one of the at least two shield-connecting members has an axial length of less than or equal to one third of a distance between the pair of conductive loop members in the direction of the common longitudinal axis. By that, a beneficially large dimension of the at least one installation space in the axial direction can be accomplished. In particular, the at least two axially arranged conductive members that are axially arranged in an aligned manner may have different dimensions in the axial direction.

In yet another preferred embodiment, at least four of the axially arranged conductive members of the plurality of axially arranged conductive members are pairwise axially arranged in an aligned manner at different azimuthal positions within the range between the two different azimuthal positions of the at least two interconnecting members, and electrically serve as shield-connecting members. In this way, a beneficially large dimension of the at least one installation space in the azimuthal direction about the common longitudinal axis can be accomplished.

The radio frequency volume coil may be designed as a whole-body coil providing sufficient space to position a major portion of the human subject of interest within the inner volume of the volume coil. The phrase "major portion", as used in this application, shall in particular be understood as at least one third of a body length of the human subject of interest.

The radio frequency volume coil may also be designed as a head coil to accommodate at least a part of the head of the human subject of interest, or as a volume coil for accommodating at least a part of a limb such as a hand or a foot, of the human subject of interest.

In one preferred embodiment, the radio frequency connection provided by each shield-connecting member comprises an impedance network. In this way, radio frequency currents flowing through the shield-connecting members can be controlled by an absolute value and a relative phase of the impedance network.

Preferably, the impedance network includes at least one lumped capacitor.

In one embodiment, the radio frequency volume coil comprises a plurality of activation ports. Each activation port is configured to receive radio frequency power of a magnetic resonance frequency for generating a radio frequency excitation field $B_1$. In particular, the radio frequency volume coil may be used in a T/R (transmit/receive) mode, as is well known in the art from the birdcage coil design.

In another aspect of the present invention, a magnetic resonance examination system is provided that is configured for acquiring magnetic resonance signals from at least a portion of a subject of interest and that comprises at least one radio frequency volume coil as disclosed herein. The magnetic resonance examination system further includes at least one auxiliary device that is at least partially positioned within the at least one installation space of the radio frequency volume coil such that a visual line aligned along two of the at least two shield-connecting members that are axially arranged in an aligned manner at an azimuthal position within the range between the two different azimuthal positions of the at least two interconnecting members intersects the at least one auxiliary device. In this way, the at least one auxiliary device can beneficially be positioned close to the radio frequency volume coil.

In one embodiment of the magnetic resonance examination system, the at least one auxiliary device comprises at least one electronic circuit board for controlling the radio frequency volume coil.

In one embodiment of the magnetic resonance examination system, the at least one auxiliary device comprises at least one RF amplifier that is configured for at least partially driving the radio frequency volume coil.

In one embodiment of the magnetic resonance examination system, the at least one auxiliary device is at least one component of a medical therapy system, including but not limited to a component of a LINAC device, a proton therapy device, a HIFU (high-intensity focused ultrasound) device or a magnetic resonance hyperthermia device, such as a radio frequency power transmission system.

In one embodiment of the magnetic resonance examination system, the at least one auxiliary device is at least one component of an additional medical imaging modality, including but not limited to a PET (positron emission tomography) device or an ultrasound device.

In one embodiment of the magnetic resonance examination system, the at least one auxiliary device is at least one component of a detection system for detecting a physiological parameter of the subject of interest. The phrase "physiological parameter", as used in this application, shall be understood particularly as a physical measure characterizing the function of at least a portion of an individual subject of interest, and shall in particular encompass parameters such as, but not limited to, respiration cycle parameters and cardiac cycle parameters. Components of a detection system for detecting the physiological parameter include, without limitation, optical or infrared cameras, temperature sensors and wireless digital or analog data communication devices.

BRIEF DESCRIPTION OF THE DRAWINGS

These and other aspects of the invention will be apparent from and elucidated with reference to the embodiments described hereinafter. Such embodiment does not necessarily represent the full scope of the invention, however, and reference is made therefore to the claims and herein for interpreting the scope of the invention.

In the drawings:

FIG. 3b is a partial electrical connecting scheme of the radio frequency volume coil pursuant to FIG. 3a.

DETAILED DESCRIPTION OF EMBODIMENTS

In the following, embodiments of a radio frequency volume coil in accordance with the invention are disclosed. The individual embodiments are described with reference to a particular figure and are identified by a prefix number of the particular embodiment. Features whose function is the same or basically the same in all embodiments are identified by reference numbers made up of the prefix number of the embodiment to which it relates, followed by the number of the feature. If a feature of an embodiment is not described in the corresponding figure depiction, or a reference number mentioned in a figure depiction is not shown in the figure itself, the description of a preceding embodiment should be referred to.

Figure 1:
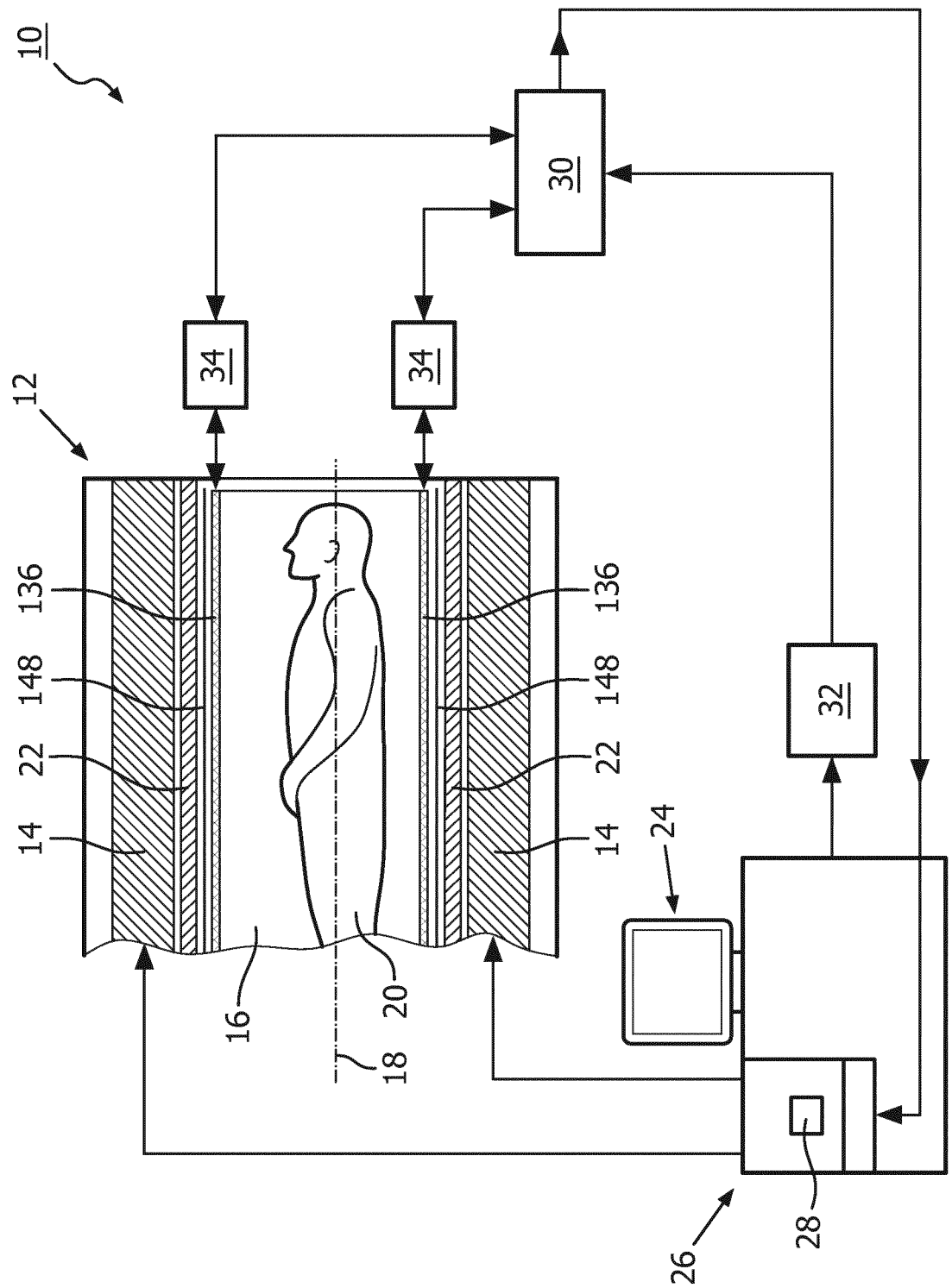
FIG. 1 shows a schematic illustration of a part of an embodiment of a magnetic resonance examination system in accordance with the invention.

FIG. 1 shows a schematic illustration of a part of an embodiment of a magnetic resonance examination system 10 in accordance with the invention, designed as a magnetic resonance imaging system configured for acquiring magnetic resonance images of at least a portion of a subject of interest 20, usually a patient. The magnetic resonance imaging system comprises a scanner unit 12 having a main magnet 14. The main magnet 14 has a central bore that provides an examination space 16 around a center axis 18 for the subject of interest 20 to be arranged within at least during examination, and is further provided for generating a static magnetic field $B_0$ at least in the examination space 16. For clarity reasons, a customary table for supporting the subject of interest 20 has been omitted in FIG. 1. The static magnetic field $B_0$ defines an axial direction of the examination space 16, aligned in parallel to the center axis 18.

Further, the magnetic resonance imaging system comprises a magnetic gradient coil system 22 configured for generating gradient magnetic fields superimposed to the static magnetic field $B_0$. The magnetic gradient coil system 22 is concentrically arranged within the bore of the main magnet 14.

The magnetic resonance imaging system comprises a control unit 26 configured to control functions of the magnetic resonance imaging system 10. The control unit 26 includes a human interface device 24 formed by a monitor unit having a touch-sensitive screen and a keyboard.

Furthermore, the magnetic resonance imaging system includes a magnetic resonance radio frequency transmission device for generating and applying a radio frequency magnetic excitation field $B_1$ of a magnetic resonance frequency during radio frequency transmit phases to nuclei of or within the subject of interest 20 for the purpose of magnetic resonance examination. The magnetic resonance radio frequency transmission device comprises a radio frequency volume coil 136 designed as a whole-body coil and two radio frequency amplifier units 34.

Each radio frequency amplifier unit 34 is configured for receiving radio frequency power, controlled by the control unit 26, via a radio frequency switching unit 30 from a radio frequency transmitter 32 of the magnetic resonance radio frequency transmission device, for amplifying the received radio frequency power, and for providing the amplified radio frequency power of the magnetic resonance frequency to the radio frequency volume coil 136 during the radio frequency transmit phases. During radio frequency receive phases, the radio frequency switching unit 30 directs the magnetic resonance signals from the radio frequency volume coil 136 to a signal processing unit 28 residing in the control unit 26. The signal processing unit 28 is configured for processing acquired magnetic resonance signals to generate scanning images represented by magnetic resonance images of the portion of the subject of interest 20.

The radio frequency volume coil 136 is provided for applying a radio frequency magnetic excitation field $B_1$ to the examination space 16 during radio frequency transmit phases to excite nuclei of or within the subject of interest 20. The radio frequency volume coil 136 is also configured for receiving magnetic resonance signals during radio frequency receive phases from the nuclei of or within the portion of the subject of interest 20 that have been excited by applying the radio frequency magnetic excitation field $B_1$. In an operational state of the magnetic resonance imaging system, radio frequency transmit phases and radio frequency receive phases are taking place in a consecutive manner.

Figure 2A:
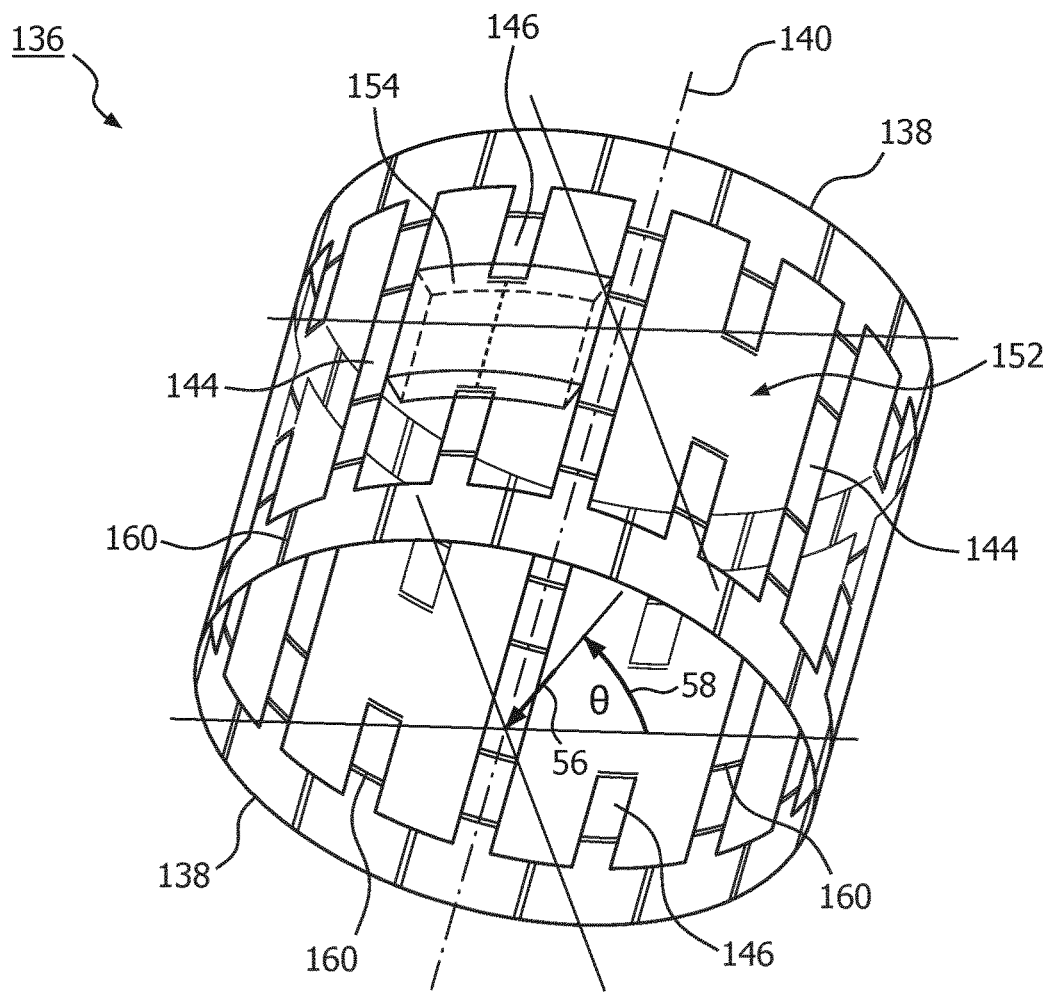
FIG. 2a shows a schematic 3D perspective view of the radio frequency volume coil of the magnetic resonance imaging system pursuant to FIG. 1.

A schematic 3D perspective view of the radio frequency volume coil 136 is provided by FIG. 2a. The radio frequency volume coil 136 includes a pair of circular radio frequency conductive loop members 138 spaced along a common longitudinal axis 140, and a plurality of axially arranged radio frequency conductive members that are electrically connected to at least one of the radio frequency conductive loop members 138. Each one of the circular radio frequency conductive loop members 138 is arranged to lie within a different plane, wherein the planes are spaced apart and arranged in parallel.

In the operational state, the common longitudinal axis 140 is arranged concentrically within the bore of the main magnet 14 such that the common longitudinal axis 140 and the center axis 18 of the scanner unit 12 coincide (FIG. 1).

The radio frequency volume coil 136 includes a cylindrical, metallic radio frequency shield 148 that is arranged concentrically to and towards the magnetic gradient coil system 22, and around the pair of radio frequency conductive loop members 138 and the plurality of axially arranged radio frequency conductive members.

The radio frequency volume coil 136 is adapted from a birdcage coil design, which is known in the art. Although the radio frequency volume coil 136 presented in FIG. 2a is adapted from a band-pass type birdcage coil, and comprises capacitors 160 between segments of the two radio frequency conductive loop members 138 as well as in the axially arranged radio frequency conductive members, it will be appreciated by those skilled in the art that the invention is also applicable to a radio frequency volume coil adapted from a high-pass type birdcage coil having capacitors in the two conductive loop elements spaced along a common longitudinal axis, or from a low-pass type birdcage coil having capacitors in the axially arranged radio frequency conductive members connecting the spaced two conductive loop members. The capacitors 160 of the radio frequency volume coil 136 are indicated in FIG. 2a by crosslines.

At the location of at least one of the capacitors 160, the radio frequency volume coil 136 comprises a local detuning circuit as known in the art for detuning or switching off the radio frequency volume coil 136 in case of employing the radio frequency volume coil 136 as a radio frequency transmit coil in combination with at least one local radio frequency receive coil or at least one local radio frequency transmit/receive coil that is located in close proximity on or under the subject of interest 20.

The plurality of axially arranged radio frequency conductive members include eight axially arranged radio frequency loop coil connecting RF conductive members 144 that electrically interconnect the two conductive loop members 138. The eight RF loop coil RF conductive interconnecting members 144 are regularly spaced in an azimuthal direction 58 about the common longitudinal axis 140, such that any two loop coil interconnecting RF conductive members 144 that are adjacently arranged in the azimuthal direction 58 are positioned at two different azimuthal positions with regard to the common longitudinal axis 140, defining a range between the two different azimuthal positions of 45°.

The plurality of axially arranged radio frequency conductive members further includes sixteen axially arranged shield connecting radio frequency conductive members 146 that are pairwise axially arranged in an aligned manner at eight azimuthal positions, wherein each azimuthal position of the eight azimuthal positions lies within one of the ranges, namely exactly in a middle position, between two different azimuthal positions of two loop coil RF conductive interconnecting members 144 that are adjacently arranged in the azimuthal direction 58. Thereby, all the axially arranged radio frequency conductive members of the plurality of axially arranged radio frequency conductive members 144, 146 are regularly spaced in the azimuthal direction 58 about the common longitudinal axis 140.

The sixteen axially arranged RF shield radio frequency conductive members 146 that are pairwise axially arranged in an aligned manner electrically connect with the RF shield 148. Each shield connecting RF conductive member 146 has an axial length that is equal to one third of a distance between the pair of conductive loop members 138 in the direction of the common longitudinal axis 140 and provides a radio frequency connection for one of the two conductive loop members 138 to the radio frequency shield 148. As indicate in FIG. 1, the radio frequency shield 148 completely covers the axially arranged radio frequency conductive members in a radial direction 56 perpendicularly arranged to and pointing towards the common longitudinal axis 140.

Figure 2B:
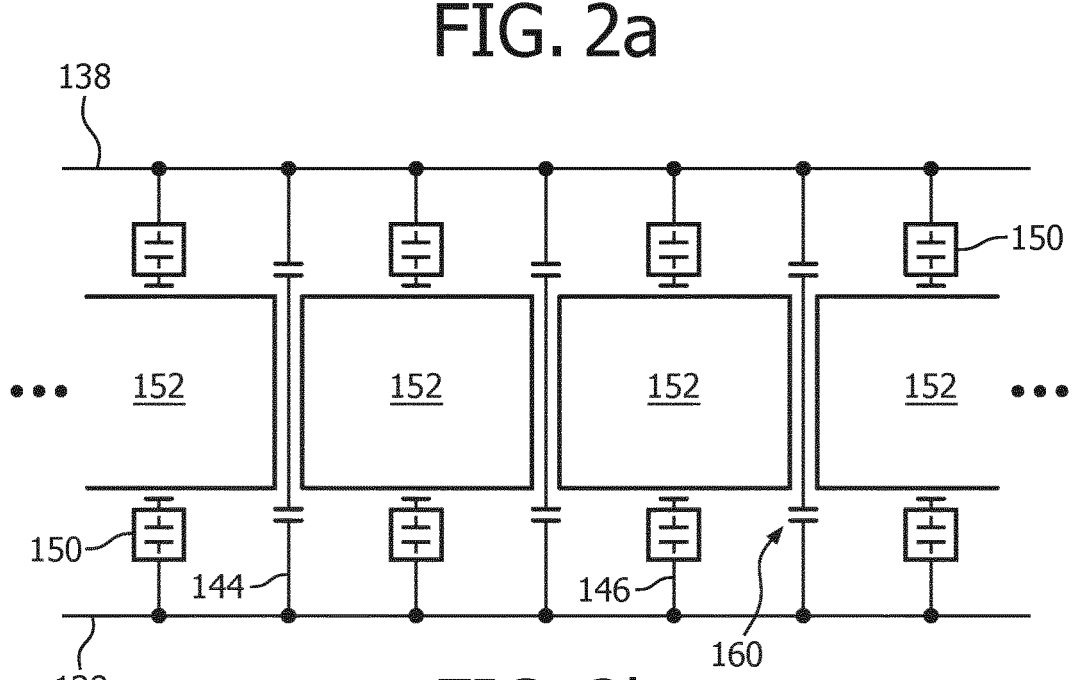
FIG. 2b is a partial electrical connecting scheme of the radio frequency volume coil pursuant to FIG. 2a, FIG. 3a shows an alternative radio frequency volume coil in accordance with the invention in a schematic 3D perspective view.

The radio frequency connection provided by each one of the sixteen shield-connecting RF conductive members 146 comprises an impedance network 150. Each one of the impedance networks 150 includes a lumped capacitor, as is indicated in the partial electrical connecting scheme of the radio frequency volume coil 136 shown in FIG. 2b. The preferred mode of operation of the radio frequency volume coil 136 is a resonant mode in which a current distribution in the axially arranged radio frequency conductive members is proportional to sin θ or cos θ, respectively, wherein θ denotes the azimuthal angle with regard to the common longitudinal axis 140. For facilitating this mode of operation, the impedance network 150 of each of the shield-connecting members 146 is designed to adapt their electrical impedance to an electrical impedance of the RF loop coil RF conductive interconnecting members 144.

In one embodiment, at least one of the axially arranged radio frequency conductive members may be formed by a strip line. In that case, an electrical impedance of the at least one axially arranged radio frequency conductive member can at least partially be adapted by modifying a geometrical dimension, for instance a width, of the strip line.

The radio frequency volume coil 136 provides sufficient space to position a major portion of the human subject of interest 20 within an inner volume of the radio frequency volume coil 136, which is defined as a space surrounded by the pair of radio frequency conductive loop members 138 and the plurality of axially arranged conductive members.

The radio frequency volume coil 136 comprises two activation ports (not shown). Each one of the activation ports is configured to receive radio frequency power supplied by one of the of radio frequency amplifier units 134 for generating the radio frequency magnetic excitation field $B_1$. The radio frequency power can be supplied as a continuous wave or as a plurality of individual pulses with arbitrary pulse shape and modulation in phase, amplitude and frequency.

Due to the arrangement of the plurality of axially arranged radio frequency conductive members, the radio frequency volume coil 136 provides eight installation spaces 152 within the inner volume of the radio frequency volume coil 136. Each one of the eight installation spaces 152 is accessible between the axially arranged loop coil interconnecting radio frequency conductive members 144 from outside the radio frequency volume coil 136 at least in the radial direction 56 with regard to the common longitudinal axis 140 within the range between the two different azimuthal positions of two loop coil interconnecting RF conductive members 144 adjacently arranged in the azimuthal direction 58, and within a range of the axial direction between axial positions of ends of the shield-connecting conducting members 146 that are distal to the conductive loop member 138 they are connected to.

Figure 3A:
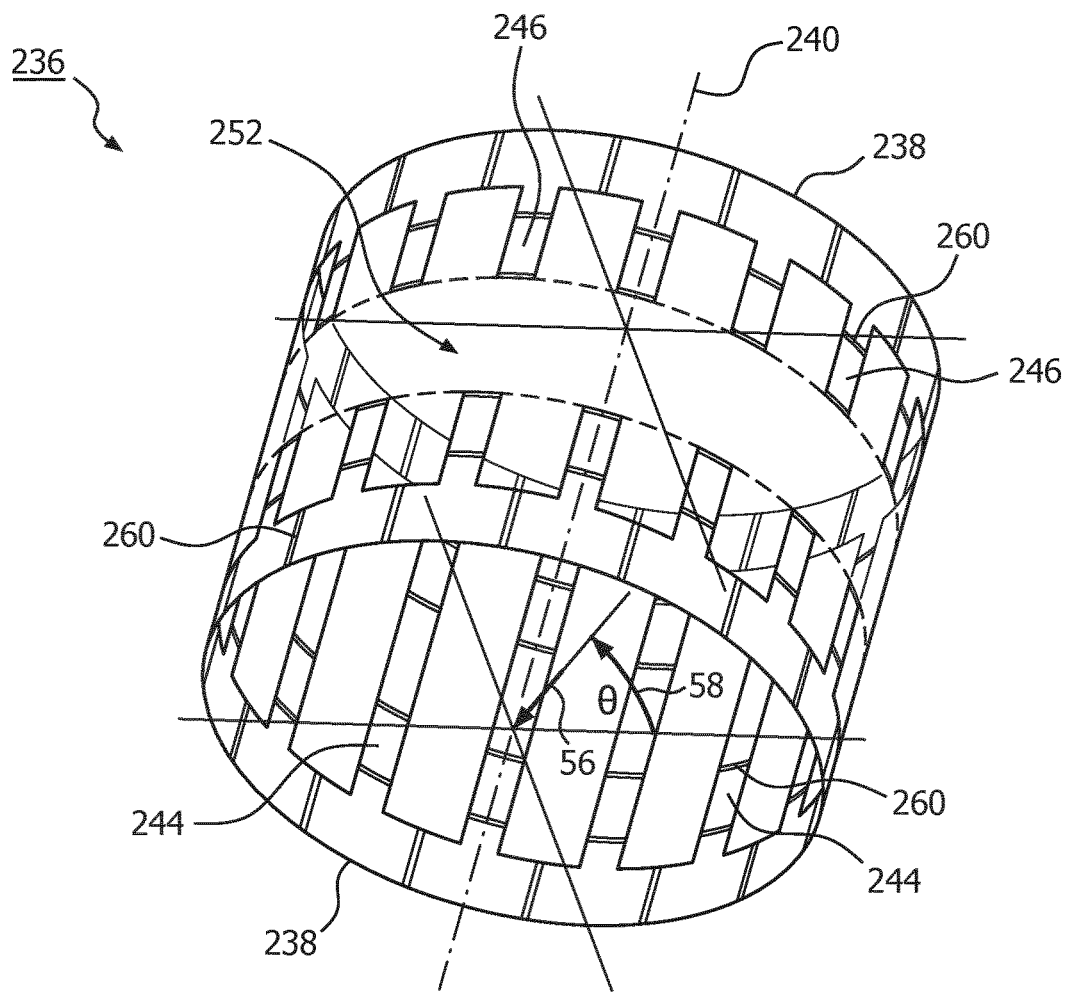

FIG. 3a shows an alternative radio frequency volume coil 236 in accordance with the invention in a schematic 3D perspective view. Only those features that differ from the first embodiment will be described. As for features that are common to both embodiments, reference is made to the description of the first embodiment.

The radio frequency volume coil 236 shown in FIG. 3a comprises a plurality of eight axially arranged loop coil interconnecting radio frequency conductive members 244 that electrically interconnect the two conductive loop members 238 as well as in the first embodiment of radio frequency volume coil 136. In contrast to the latter, the plurality of eight loop coil interconnecting RF conducting members 244 is arranged in a regularly spaced manner in the azimuthal direction 58 about a common longitudinal axis 240, such that any two loop coil interconnecting RF conducting members 244 that are adjacently arranged in the azimuthal direction 58 are positioned at two different azimuthal positions with regard to the common longitudinal axis 240, defining a range between the two different azimuthal positions of 22.5°. In this way, the loop coil interconnecting RF conducting members 244 of the radio frequency volume coil 236 are arranged within a first angular range of 180° in the azimuthal direction 58.

Further sixteen axially arranged radio frequency shield connecting RF conductive members 246 that are pairwise axially arranged in an aligned manner at eight azimuthal positions that differ by integer multiples of 22.5°. The eight azimuthal positions are regularly spaced within a second angular range of 180° in the azimuthal direction 58, wherein the first angular range and the second angular range are complementary and constitute a complete circle. Thereby, all the axially arranged radio frequency conductive members 244, 246 of the plurality of axially arranged radio frequency conductive members are regularly spaced in the azimuthal direction 58 about the common longitudinal axis 240.

Figure 3B:
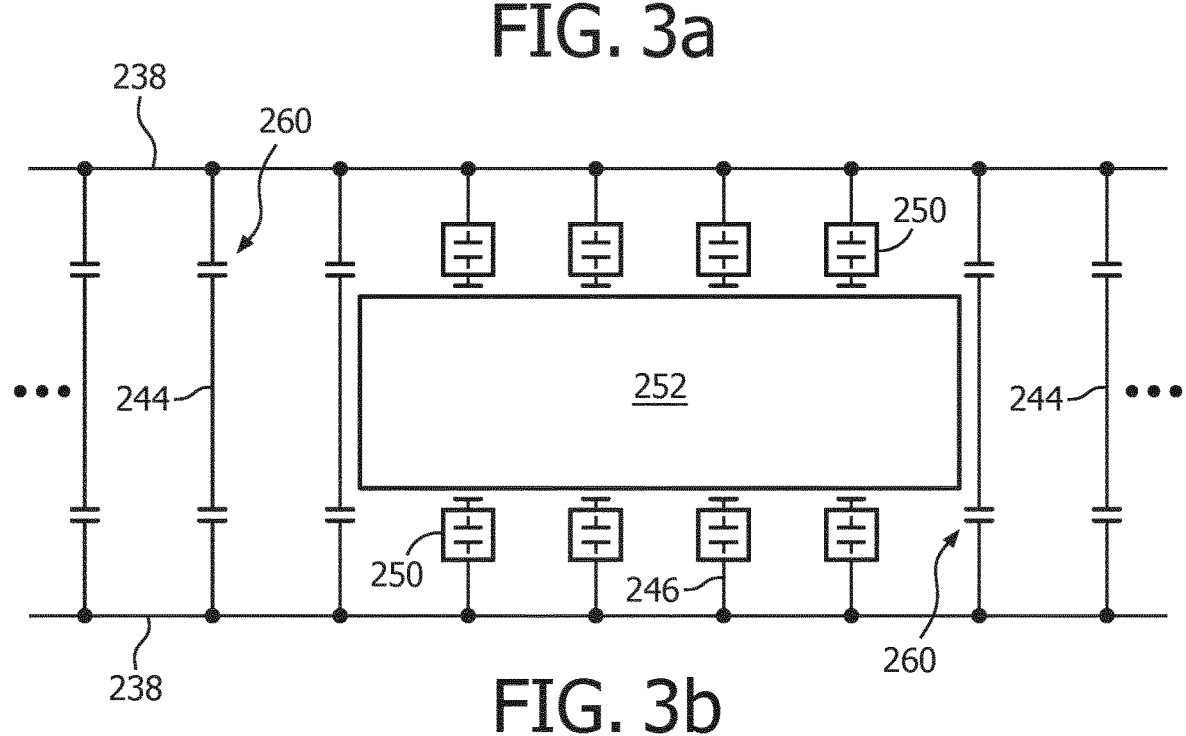

In the same manner as in the first embodiment, the radio frequency connection provided by each one of the sixteen RF shield-connecting RF conducting members 246 comprises an impedance network 250 including a lumped capacitor, as is indicated in the partial electrical connecting scheme of the radio frequency volume coil 236 shown in FIG. 3b.

Due to this arrangement of the plurality of axially arranged radio frequency conductive interconnecting members 244, 246, the radio frequency volume coil 236 provides one large installation space 252 within the inner volume of the radio frequency volume coil 236. The installation space 252 is accessible between the axially arranged conductive members from outside the radio frequency volume coil 236 at least in the radial direction 56 with regard to the common longitudinal axis 240 within the range of 180° between two azimuthal positions of a first loop coil interconnecting RF conductive member 244 and a last loop coil interconnecting RF conductive member 244, of the plurality of eight loop coil interconnecting RF conductive members 244, that are adjacently arranged in the azimuthal direction 58, and within a range of the axial direction between axial positions of ends of the RF shield connecting RF conductive members 246 that are distal to the conductive loop member 238 they are connected to.

The installation spaces 152, 252 described for the first and the second embodiment of a radio frequency volume coil 136, 236 in accordance with the invention provides options for positioning auxiliary devices 154 at least partially within the installation space 152, 252, for instance a radio frequency amplifier or a digital data communication device of the magnetic resonance examination system 10.

The installation space 252 provided by the second embodiment of the radio frequency volume coil 236 (FIG. 3a) is especially appropriate to partially accommodate an auxiliary device formed by a component of a medical therapy system such as a component of a LINAC device, a proton therapy device, a HIFU (high-intensity focused ultrasound) device or a magnetic resonance hyperthermia device, such as a radio frequency power transmission system. It would also be appropriate to partially accommodate an auxiliary device formed by a component of an additional medical imaging modality, such as a PET detection ring or an ultrasound device. In these cases, the radio frequency volume coil 236 is beneficial due to a low inherent attenuation for radiation, for instance γ-radiation.

The installation spaces 152 provided by the first embodiment of the radio frequency volume coil 136 (FIG. 2a) are especially appropriate to partially accommodate an auxiliary device 154 formed by a component of a detection system for detecting a physiological parameter of the subject of interest 20, such as an optical camera (visible range of infra-red range) or a radar detector device.

Each one of the auxiliary devices 154 is positioned such that a visual line aligned along two RF shield connecting RF conductive members 146, 246 that are axially arranged in an aligned manner at an azimuthal position within the range between two different azimuthal positions of two loop coil interconnecting RF conductive members 144, 244 intersects the auxiliary device 154, as indicated in FIGS. 2a and 3a by a dotted line.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

| REFERENCE SYMBOL LIST | |
|---|---|
| 10 | magnetic resonance examination system |
| 12 | scanner unit |
| 14 | main magnet |
| 16 | examination space |
| 18 | center axis |
| 20 | subject of interest |
| 22 | magnetic gradient coil system |
| 24 | human interface device |
| 26 | control unit |
| 28 | signal processing unit |
| 30 | radio frequency switching unit |
| 32 | radio frequency transmitter |
| 34 | radio frequency amplifier unit |
| 36 | radio frequency volume coil |
| 38 | radio frequency conductive loop member |
| 40 | common longitudinal axis |
| 44 | interconnecting member |
| 46 | shield-connecting member |
| 48 | radio frequency shield |
| 50 | impedance network |
| 52 | installation space |
| 54 | auxiliary device |
| 56 | radial direction |
| 58 | azimuthal direction |
| 60 | capacitor |
| $B_0$ | static magnet field |
| $B_1$ | radio frequency magnetic excitation field |

The invention claimed is:

1. A radio frequency volume coil for use in a magnetic resonance examination system, for at least one of generating a radio frequency magnetic excitation field B1 to be applied to nuclei of or within a subject of interest to be examined and acquiring magnetic resonance signals from the excited nuclei, the radio frequency volume coil comprising:
   a radio frequency shield,
   a pair of radio frequency conductive loop members spaced along a common longitudinal axis,
   a plurality of radio frequency shield connecting radio frequency conductive members axially arranged and electrically connected to one of the radio frequency conductive loop members, and to the radio frequency shield, each providing a radio frequency connection for one of the two radio frequency conductive loop members to the radio frequency shield,
   at least two axially arranged loop coil interconnecting radio frequency conductive members interconnecting the pair of radio frequency conductive loop members, the at least two axially arranged loop coil interconnecting radio frequency conductive members being positioned at two different azimuthal positions with regard to the common longitudinal axis, defining a range between the two different azimuthal positions that is less than or equal to 180°, and
   at least one installation space within an inner volume of the radio frequency volume coil that is accessible between the axially arranged loop coil interconnecting radio frequency conductive members from outside the radio frequency volume coil at least in a radial direction with regard to the common longitudinal axis within a range between the two different azimuthal positions of two adjacent loop coil interconnecting radio frequency conductive members, and within a range of the axial direction between axial positions of ends of the radio frequency shield-connecting radio frequency conducting members that are distal to the radio frequency conductive loop members they are connected to.

2. The radio frequency volume coil as claimed in claim 1, wherein the plurality of axially arranged loop coil interconnecting radio frequency conductive members are regularly spaced in the azimuthal direction about the common longitudinal axis.

3. The radio frequency volume coil as claimed in claim 1, wherein at least one of the at least two radio frequency shield-connecting radio frequency conductive members has an axial length of less than or equal to one third of a distance between the pair of radio frequency conductive loop members in the direction of the common longitudinal axis.

4. The radio frequency volume coil as claimed in claim 1, wherein at least four of the plurality of axially arranged radio frequency shield coil connecting radio frequency conductive members are pairwise axially arranged in an aligned manner at different azimuthal positions within the range between the two different azimuthal positions of the at least two interconnecting members.

5. The radio frequency volume coil as claimed in claim 1, designed as a whole-body coil providing sufficient space to position a major portion of a human subject of interest within the inner volume of the radio frequency volume coil.

6. The radio frequency volume coil as claimed in claim 1, further including:
   impedance networks interconnecting the radio frequency conductive loop coils with the axially arranged radio frequency shield connecting radio frequency conductive members and the axially arranged loop coil interconnecting radio frequency conductive members.

7. The radio frequency volume coil as claimed in claim 6, wherein the impedance network includes at least one lumped capacitor.

8. The radio frequency volume coil as claimed in claim 1, wherein the axially arranged radiofrequency shield connecting radio frequency conductive members and the axially arranged loop coil interconnecting radio frequency conductive members are connected in alternating azimuthal positions to each of the radio frequency loop coils.

9. A magnetic resonance examination system that is configured for acquiring magnetic resonance signals from at least a portion of the subject of interest, comprising:
   at least one radio frequency volume coil as claimed in claim 1, and
   at least one auxiliary device that is at least partially positioned within the at least one installation space such that a visual line aligned along two of the at least two radio frequency shield-connecting radio frequency conductive members such that the at least one auxiliary device is disposed axially arranged in an aligned manner between the at least two loop coil interconnecting radio frequency conductive members.

10. The magnetic resonance examination system as claimed in claim 9, wherein the at least one auxiliary device is at least one component of a medical therapy system.

11. The magnetic resonance examination system as claimed in claim 9, wherein the at least one auxiliary device is at least one component of an additional medical imaging modality.

12. The magnetic resonance examination system as claimed in claim 9, wherein the at least one auxiliary device is at least one component of a detection system for detecting a physiological parameter of the subject of interest.

13. A radio frequency (RF) volume coil for a magnetic resonance (MR) system for at least one of applying RF signals to and receiving RF signals from a subject in an inner volume of the RF volume coil, the RF volume coil comprising:
- a first loop coil;
- a second loop coil disposed parallel to and axially displaced from the first loop coil;
- a plurality of axially extending loop coil interconnecting members each pair including a first shield connection member connected at a first end to the first loop coil and at a second end to the second loop coil;
- an RF shield disposed annularly around the first loop coil, the second loop coil and the loop coil interconnecting members;
- a plurality of pairs of first shield connecting members connected at a first end to the first loop coil and at a second end to the RF shield and second shield connecting members connected at a first end to the second loop coil and at a second end of the RF shield, each of the plurality of pairs of shield connecting members being axially aligned, extending axially towards each other, and having an axial length less than or equal to one third of a distance between the first and second loop coils; and
- at least one installation space defined in the inner volume of the RF volume coil axially between the second ends of one or more of the pairs of first and second shield connecting members and azimuthally between two adjacent ones of the loop coil interconnecting members, the at least one installation space being assessible radially from outside the RF volume coil.

14. The RF volume coil as claimed in claim 13, wherein the first loop coil, the second loop coil, the plurality of axially extending loop coil interconnecting members, and the plurality of first and second pairs of shield connecting members being radio frequency conductive.

15. The RF volume coil as claimed in claim 13, wherein the loop coil interconnecting members and the pairs of first and second shield connecting members are alternately connected azimuthally with the first and second loop coils at regularly spaced in an azimuthal direction about a common longitudinal axis.

16. The RF volume coil as claimed in claim 13, wherein a plurality of the pairs of shield connecting members are connected to the loop coils adjacent to each other in an azimuthal direction around the common axis.

17. A magnetic resonance examination system configured to acquire magnetic resonance signals from at least a portion of the subject comprising:
- at least one RF volume coil as claimed in claim 13; and
- at least one auxiliary device that is at least partially disposed within at least one installation space.

* * * * *